to cell-surface ovine prion protein", Biochem. J., 381, p. 221-229 (2004).
United States Patent
Jackman et al.

(10) Patent No.: US 7,601,506 B2
(45) Date of Patent: Oct. 13, 2009

(54) IDENTIFICATION OF LEUCOCYTES BEARING DIAGNOSTIC MARKERS FOR TRANSMISSIBLE SPONGIFORM ENCEPHALOPATHIES

(75) Inventors: Roy Jackman, Derbyshire (GB); Linda Ann Terry, Berkshire (GB); Sally Jane Everest, Surrey (GB)

(73) Assignee: IDEXX Laboratories, Inc., Westbrook, ME (US)

( * ) Notice: Subject to any disclaimer, the term of this patent is extended or adjusted under 35 U.S.C. 154(b) by 14 days.

(21) Appl. No.: 11/494,964

(22) Filed: Jul. 28, 2006

(65) Prior Publication Data

US 2008/0026364 A1 Jan. 31, 2008

(51) Int. Cl.
*G01N 33/53* (2006.01)
(52) U.S. Cl. ................ 435/7.1; 436/501; 436/536; 436/513; 436/547
(58) Field of Classification Search .................. None
See application file for complete search history.

(56) References Cited

U.S. PATENT DOCUMENTS

| 7,041,807 | B1 | 5/2006 | Cashman et al. |
| 2004/0072236 | A1 | 4/2004 | Cashman et al. |
| 2005/0239139 | A1 | 10/2005 | Estey et al. |
| 2008/0113387 | A1 | 5/2008 | Bujdoso |

FOREIGN PATENT DOCUMENTS

| EP | 1 215 497 A1 | 6/2002 |
| WO | WO 00/78344 A1 | 12/2000 |
| WO | WO 03/073106 | 9/2003 |
| WO | WO2006/079805 | 3/2006 |

OTHER PUBLICATIONS

Nouanthong et al (2006) Clinical and Vaccine Immunology. 13(5): 598-601.*
Carmona et al (2005) Journal of General Virology. 86: 3425-3431.*
Morel, et al., "Selective and efficient Immunoprecipitation of the Disease-associated form of the Prion Protein can be Mediated by Nonspecific Interactions between Monoclonal Antibodies and Scrapie-associated Fibrils", The Journal of Biological Chemistry, vol. 279, No. 29, pp. 30143-30149 (2004).
Rhie, et al., "Characterization of 2'-Fluoro-RNA Aptamers that Bind Preferentially to Disease-associated Conformations of Prion Protein and Inhibit Conversion", The Journal of Biological Chemistry, vol. 278, No. 41, pp. 39697-39705 (2003).
Sayer, et al., "Structural Determinants of Conformationally Selective, Prion-binding Aptamers", The Journal of Biological Chemistry, vol. 279, No. 13, pp. 13102-13109 (2004).
Tayebi, et al., "Disease-Associated Prion Protein Elicits Immunoglobulin M Responses In Vivo", Molecular Medicine, vol. 10, No. 7-12, p. 104-111 (2004).
Zou, et al., "Antibody to DNA detects scrapie but not normal prion protein", PNAS, vol. 101, No. 5, p. 1380-1385 (2004).
Thackray, et al., "Conformational variation between allelic variants to cell-surface ovine prion protein", Biochem. J., 381, p. 221-229 (2004).
Hunter, et al., "Transmission of prion diseases by blood transfusion", Journal of General Virology, 83, p. 2897-2905 (2002).
Coulthart, et al., "Variant Creutzfeldt-Jakob disease: a summary of current scientific knowledge in relation to public health", CMAJ, 165(1):51-58 (2001).
Cashman, "A prion primer", Can Med. Assoc. J., 157(10:1381-1385 (1997).
Will, et al., "A new variant of Creutzfeldt-Jakob disease in the UK", The Lancet, vol. 347, p. 921-925 (1996).
Collinge, "Variant Creutzfeldt-Jakob disease", The Lancet, vol. 354, p. 317-323 (1999).
Paramithiotis, et al., "A prion protein epitope selective for the pathologically misfolded conformation", nature Medicine, vol. 9, No. 7, pp. 893-899 (2003).
Schmerr, et al., "Use of capillary electrophoresis and fluorescent labeled peptides to detect the abnormal prion protein in the blood of animals that are infected with a transmissible spongiform encephalopathy". Journal of Chromatography A, 853 p. 207-214 (1999).
Korth, et al., "Prion ($PrP^{SC}$)-specific epitope defined by a monoclonal antibody", Nature, vol. 390, p. 74-77 (1997).
Proske, et al., "Prion-Protein-Specific Aptamer Reduces $PrP^{SC}$ Formation", ChemBioChem, 3, 717-725 (2002).
Sekiya, et al., "In vitro selection of RNA aptamers against cellular and abnormal isoform of mouse prion protein", Nucleic Acids Symposium Series No. 49, 361-362 (2005).
Aguzzi, et al., "Progress and problems in the biology, diagnostics, and therapeutics of prion diseases", The Journal of Clinical Investigation, vol. 114, No. 2, pp. 153-159(2004).
Schmerr, et al., "Use of capillary electrophoresis and fluorescent labeled peptides to detect the abnormal prion protein in the blood of animals that are infected with a transmissible spongiform encephalopathy", Journal of Chromatography A, 853 (1999) 207-214.
Parish, et al., "Latex Bead Rosetting Method for Cell Surface Antigens", Journal of Immunological Methods, 53 (1982) 367-372.
Ironside, et al., "Variant Creutzfeldt-Jakob disease and its transmission by blood", Journal of Thrombosis and Haemostasis 1:1479-1486, (2006).
International Search Report for Corresponding PCT Application No. PCT/US2007/074454 dated Oct. 29, 2007.
Deleault, et al., "RNA molecules stimulate prion protein conversion", Nature, vol. 425, pp. 717-720 (2003).

(Continued)

*Primary Examiner*—Gary B. Nickol
*Assistant Examiner*—Michelle Horning
(74) *Attorney, Agent, or Firm*—McDonnell Boehnen Hulbert & Berghoff LLP

(57) ABSTRACT

The invention provides a simple method for diagnosing a non-symptomatic or symptomatic human or animal with transmissible spongiform encephalopathy.

6 Claims, 3 Drawing Sheets

OTHER PUBLICATIONS

Weiss, et al., "RNA Aptamers Specifically Interact with the Prion Protein PrP", Journal of Virology, vol. 71, No. 11, pp. 8790-8797 (1997).

Zanusso, et al., "Prion protein expression in different species: Analysis with a panel of new mAbs", Proc. Natl. Acad. Sci. USA, vol. 95, pp. 8812-8816 (1998).

Féraudet, et al., "Screening of 145 Anti-PrP Monoclonal Antibodies for Their Capacity to Inhibit PrPSc Replication in Infected Cells", The Journal of Biological Chemistry, vol. 280, No. 12, pp. 11247-11258 (2005).

* cited by examiner

1A. Scrapie Positive        1B. Scrapie Negative

US 7,601,506 B2

IDENTIFICATION OF LEUCOCYTES BEARING DIAGNOSTIC MARKERS FOR TRANSMISSIBLE SPONGIFORM ENCEPHALOPATHIES

BACKGROUND OF THE INVENTION

Transmissible spongiform encephalopathies are a group of rapidly progressive, fatal, and untreatable neurodegenerative syndromes. Human transmissible spongiform encephalopathies include, e.g., classical Creutzfeldt-Jakob disease (CJD), which has sporadic, iatrogenic, and familial forms, and variant CJD (vCJD) (Will et al., *Lancet* 347:921-25, 1996; Collinge, *Lancet* 354:317-23, 1999; Cashman, *Can. Med. Assoc. J.* 157:1381-5, 1997; Coulthart & Cashman, *Can. Med. Assoc. J.* 165:51-8, 2001); and kuru. Scrapie affects sheep and goats. Additionally, mink, deer, elk, and bovines are affected by transmissible spongiform encephalopathy. Bovine Spongiform Encephalopathy (BSE) has been a major economic and animal welfare epizootic in Europe since 1986 and has been implicated as the causative agent of human vCJD.

Prions are infectious agents that are associated with the transmissible spongiform encephalopathies noted above. The prion diseases are characterized by spongiform change (e.g., microcavitation of the brain, usually predominant in gray matter), neuronal cell loss, astrocytic proliferation disproportionate to neuronal loss, and accumulation of an abnormal amyloidogenic protein, sometimes in discrete plaques in the brain.

TSEs are associated with accumulation of an abnormal form of a protein ($PrP^{Sc}$) naturally produced by the host, $PrP^c$. $PrP^{Sc}$ can accumulate in the brain and peripheral lymphoid system as amyloid plaques or deposits. $PrP^c$ expression occurs in cells of many other tissues and fluids in the body (e.g. blood leucocytes, heart) but no plaque deposits have yet been detected in TSEs.

Antibodies that are specific for an abnormal isoform of a prion protein are known in the art (Paramithiotis et al. 2003. *Nature Medicine.* 9:893-899). However, except for Schmerr et al. 1999. *J. Chromatog. A* 853: 207-214) there are no blood tests for TSEs available at present. Additionally, no simple tests for TSEs are available.

TSE infectivity has been demonstrated in the blood and leucocytes of sheep infected with scrapie and in bovine spongiform encelphalopathy (BSE). See, e.g., Hunter et al. 2002. *J. Gen. Virol.* 83:2897-2905). $PrP^{Sc}$ has been demonstrated in leucocyte preparations of scrapie infected blood. See, e.g., Schmerr et al., 1999. *J. Chromatog. A* 853: 207-214.

The availability of methods that can distinguish $PrP^{Sc}$ from $PrP^c$ would be of great value in development of a test for prion infection in blood or other tissues accessible to sampling. Accordingly, a need exists in the art for simple testing of samples for the presence of prions.

SUMMARY OF THE INVENTION

One embodiment of the invention provides a method for diagnosing transmissible spongiform encephalopathy (TSE) or infection with a TSE agent. The method comprises contacting leucocytes from a subject, with an antibody, ligand or aptamer specific for or selective for $PrP^{Sc}$, contacting the leucocytes with anti-immunoglobulin coated beads and examining the beads and leucocytes for a rosetting effect. A rosetting effect indicates a diagnosis of TSE. The antibody specific for $PrP^{Sc}$ can be an anti-YYR antibody. The antibody can be IgG and the anti-immunoglobulin can be anti-IgG. The antibody can be IgM and the anti-immunoglobulin can be anti-IgM. The antibody can be produced by hybridoma ATCC PTA-7393. The subject may have no TSE symptoms. The subject can be a human, non-human primate, ovine, bovine, deer, elk, murine, or mink.

Another embodiment of the invention provides a method for diagnosing transmissible spongiform encephalopathy (TSE). The method comprises contacting leucocytes from a subject with beads, wherein the beads are coated with antibodies, ligands, or aptamers that are specific for or selective for $PrP^{Sc}$, and examining the beads and leucocytes for a rosetting effect. A rosetting effect indicates a diagnosis of TSE.

The invention, therefore, provides a very simple method for the detection of $PrP^{Sc}$ and the diagnosis of TSE.

DETAILED DESCRIPTION OF THE INVENTION

Figure 1:
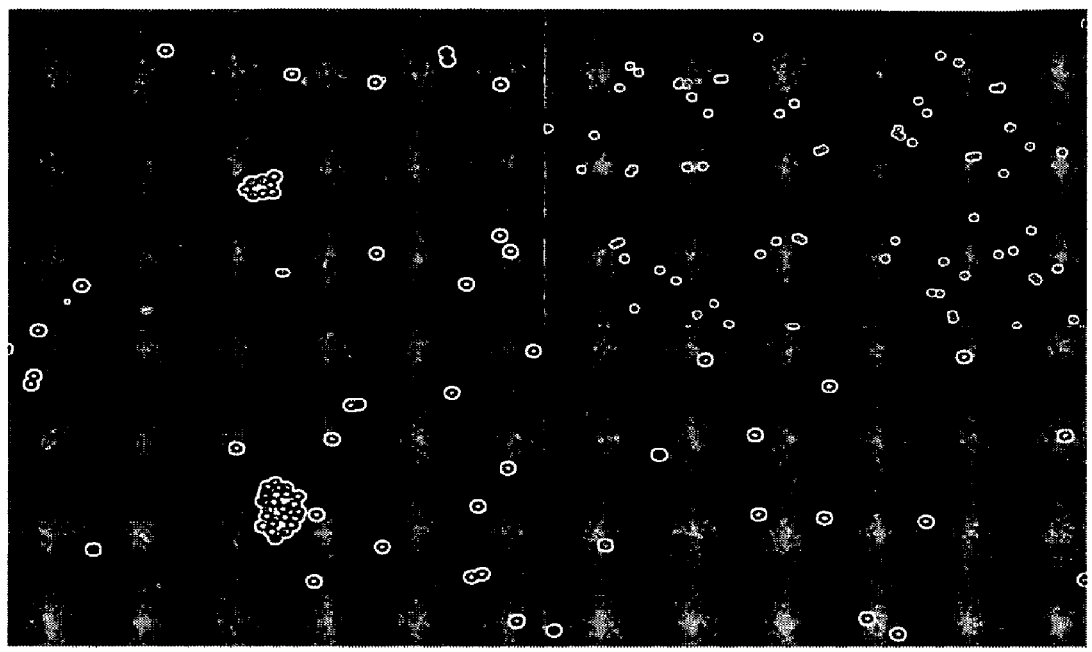
FIG. 1A-B shows a photograph of a light microscope slide of leucocytes from one animal from the heavily scrapie-infected Ripley flock and one animal from a negative control flock at ×20 and ×40 magnification. (A) 31A.8 binding demonstrated by the rosetting of beads as they bound to cell surface $PrP^{Sc}$ on scrapie positive leucocytes. (B) No binding of 31A.8 beads to cells in scrapie negative blood as shown by the absence of rosettes.

In one embodiment of the invention antibodies are employed that specifically and stably bind to an abnormal isoform of a prion protein, i.e., $PrP^{Sc}$. An antibody of the invention can be a polyclonal antibody, a monoclonal antibody, a single chain antibody (scFv), or an antigen-binding portion of an antibody. Antigen-binding portions of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, F(ab')$_2$ and F$_v$ fragments.

An antibody of the invention can be any antibody class, including for example, IgG, IgM, IgA, IgD and IgE. An antibody or antigen-binding portion thereof can bind to an epitope of an abnormal isoform of a prion protein. An antibody can be made in vivo in suitable laboratory animals or in vitro using recombinant DNA techniques. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992).

Examples of antibodies specific for $PrP^{Sc}$ and their production are described in, e.g., Paramithiotis et al., (2003) *Nature Med.* 9:893; U.S. Publ. No. 2004/0072236; U.S. application Ser. No. 09/602,775; Thackray et al., *Biochem. J.* (2004) 381, 221-229. Other antibodies that are claimed to be specific for PrP$^{Sc}$ include, for example, 15B3 (Korth et al., *Nature,* 390:74 (1997)) and OCD4 (Zou et al., *PNAS,* 101:1380 (2004)).

In one embodiment of the invention an antibody binds to a YYR epitope of a mammalian PrP$^{Sc}$ (an "anti-YYR antibody"). Antibodies generated against the prion protein motif YYR recognize the pathological isoform of the prion protein, but not the normal cellular isoform. See, e.g., Paramithiotis et al., (2003) *Nature Med.* 9:893. The YYR epitope can be part of, e.g., CYYR (SEQ ID NO:1), CYYRRYYRYY (SEQ ID NO:2); YYRRYYRYY (SEQ ID NO:3). See, e.g., U.S. Publ. 2004/0072236, filed Sep. 27, 2002; U.S. Ser. No. 09/602,775, filed Jun. 23, 2000.

"Specifically binds" or "specific for" means that an anti-PrP$^{Sc}$ antibody recognizes and binds to PrP$^{Sc}$ or a portion thereof (an antigen) with greater affinity than to PrP$^c$. Binding specifically can be tested using, for example, an enzyme-linked immunosorbant assay (ELISA), a radioimmunoassay (RIA), an immunoprecipitation assay, or a western blot assay using methodology well known in the art.

Polyclonal antibodies can be produced by administering a polypeptide to an animal, such as a human or other primate, mouse, rat, rabbit, guinea pig, goat, pig, dog, cow, sheep, donkey, or horse. Serum from the immunized animal is collected and the antibodies may be purified from the plasma by, for example, precipitation with ammonium sulfate, followed by chromatography, such as affinity chromatography. Techniques for producing and processing polyclonal antibodies are known in the art.

Monoclonal antibodies directed against an abnormal isoform of a prion protein can also be readily produced. See, e.g., Tayebi et al., Mol Med. Dec. 9, 2004. For example, normal B cells from a mammal, such as a mouse, which was immunized with an abnormal isoform of a prion protein can be fused with, for example, HAT-sensitive mouse myeloma cells to produce hybridomas. Hybridomas producing PrP$^{Sc}$-specific antibodies can be identified using RIA or ELISA and isolated by cloning in semi-solid agar or by limiting dilution. Clones producing PrP$^{Sc}$-specific antibodies are isolated by another round of screening. Monoclonal antibodies can be screened for specificity using standard techniques, for example, by binding a PrP$^{Sc}$ to a microtiter plate and measuring binding of the monoclonal antibody by an ELISA assay. Techniques for producing and processing monoclonal antibodies are known in the art. See e.g., Kohler & Milstein, *Nature,* 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., *P.N.A.S. U.S.A.* 82:8653 1985; Spria et al., *J. Immunolog. Meth.* 74:307, 1984. Monoclonal antibodies can also be prepared from a mixed parental hybridoma, for example, ovine or human B-cells and murine myeloma. See, Kitano et al., *Appl. Microbiol. Biotechnol.* 24:284-286 1986; Su et al., *Hybridoma* 19:81-87 2000. Monoclonal antibodies of the invention can also be recombinant monoclonal antibodies. See, e.g., U.S. Pat. No. 4,474,893; U.S. Pat. No. 4,816,567. Antibodies of the invention can also be chemically constructed. See, e.g., U.S. Pat. No. 4,676,980. Antibodies can also be produced from naive (non-immunized) libraries by, e.g., phage display technology, and screening for PrP-binding. Williamson et al., *J. Viro.* 72:9413-9418 1998; Prusiner et al., *Science.* 278:245-251 1997.

Antibodies of the invention can be chimeric (see, e.g., U.S. Pat. No. 5,482,856), humanized (see, e.g., Jones et al., *Nature* 321:522 (1986); Reichmann et al., *Nature* 332:323 (1988); Presta, *Curr. Op. Struct. Biol.* 2:593 (1992)), or human antibodies. Human antibodies can be made by, for example, direct immortalization, phage display, transgenic mice, or a Trimera methodology, see e.g., Reisener et al., *Trends Biotechnol.* 16:242-246 (1998).

Antibodies, ligands, and/or aptamers that bind PrP$^{Sc}$, but not to PrP$^c$ are particularly useful for detecting the presence of PrP$^{Sc}$ in a sample, such as a serum, blood, leukocyte, or tissue sample from a PrP$^{Sc}$-infected animal such as a human. An immunoassay for PrP$^{Sc}$ can utilize one antibody, aptamer, or ligand, or several antibodies, aptamers, or ligands, or a combination thereof. Antibodies, aptamers, and ligands of the invention can be labelled with any type of label known in the art, including, for example, fluorescent, chemiluminescent, radioactive, enzyme, colloidal metal, and bioluminescent labels.

In another embodiment of the invention ligands or aptamers specific for PrP$^{Sc}$ can be used in the methods of the invention. For example, aggregation of PrP$^{Sc}$ in the presence of PrP$^c$ can be achieved by contacting a sample under selective binding conditions, with a polyionic material having a binding avidity for PrP$^{Sc}$. See WO03/073106 A2 (Lane et al., "Binding of Pathological Forms of Prion Proteins"), which is incorporated by reference herein in its entirety. These polyionic materials that have a binding avidity for PrP$^{Sc}$ are "PrP$^{Sc}$ ligands." The selective binding conditions can include a discriminating agent such as laurylsarcosine. The polyionic materials, selective binding conditions, other conditions, other materials, assay methods, and other methods described in WO03/073106 can be used in the instantly disclosed methods and are specifically incorporated by reference in their entirety herein.

The materials and methods described in WO03/073106 can further be improved by the addition of a charged agent, such as charged detergent agent, for example, a zwitterionic agent to the selective binding conditions. See, U.S. Publ. 2005/0239139 (filed Apr. 5, 2005), which is incorporated by reference in its entirety herein. For example, a sample containing PrP$^{Sc}$ (and optionally PrP$^c$) can be contacted, under selective binding conditions, with a polyionic material having a binding avidity for the abnormal aggregating form of the protein, a zwitterionic agent, and a discriminating agent such as laurylsarcosine. "Selective binding" or "selective for" means that PrP$^{Sc}$ binds to a polyionic material having a binding avidity for PrP$^{Sc}$, while PrP$^c$ does not substantially bind the polyionic material.

Selective binding conditions provide conditions under which polyionic materials bind PrP$^{Sc}$ but do not substantially bind PrP$^c$. Selective binding conditions provide binding that is sufficiently strong and selective to be useful in assays for the presence of PrP$^{Sc}$. Selective binding conditions can be determined by one of skill in the art and can be obtained by, for example, suitable adjustment of the reaction conditions, particularly the presence and concentration of a discriminating agent, a charged agent such as a zwitterionic agent, the pH, and the detergency. Suitable selective binding conditions are described in, for example, WO03/073106 and in the examples of U.S. Publ. No. U.S. Publ. 2005/0239139. In one embodiment of the invention selective binding conditions comprise a pH from about 8 to about 9, and more particularly a pH from about 8.2 to about 8.6.

Binding avidity means the overall binding strength of a molecule with many binding sites with a multivalent binding agent (e.g., the polyionic material), which is in contrast to "affinity", which is the binding strength between each individual binding site of the molecule and the binding agent (e.g., the polyionic material).

Suitable polyionic materials having a binding avidity for $PrP^{Sc}$ are described in WO03/073106. A polyionic material can be protease resistant. The polyionic material can be a polyanionic material having a multiplicity of anionic groups or a polycationic material having a multiplicity of cationic groups. Anionic groups can be, for example, sulphate, carboxyl or phosphate groups. Cationic groups can be, for example, amino groups, imine groups or quaternary ammonium groups.

In one embodiment of the invention a detergent is part of the selective binding conditions and promotes selective binding either by virtue of detergency or by acting as a discriminating agent.

A charged detergent or detergent-like agent can be added to the selective binding conditions of the methods of the invention to improve sensitivity and detection of an aggregating abnormal form of a protein. A charged detergent or detergent-like agent can be an anionic, cationic, or zwitterionic detergent or detergent-like agent. A zwitterionic agent is a molecule carrying both a positive and a negative charge. Any zwitterionic agent can be used in the methods of the invention, for example, a zwitterionic agent can be, for example, ZWITTERGENT® 3-08 (n-Octyl-N,N-dimethyl-3-ammonio-1-propanesulfonate), ZWITTERGENT® 3-10 (n-Decyl-N,N-dimethyl-3-ammonio-1-propanesulfonate), ZWITTERGENT® 3-12 (n-Dodecyl-N,N-dimethyl-3-ammonio-1-propanesulfonate), ZWITTERGENT® 3-14 (n-tetradecyl-N,N-dimethyl-3-ammonio-1-propanesulfonate), ZWITTERGENT® 3-16 (n-Hexadecyl-N,N-dimethyl-3-ammonio-1-propanesulfonate). In one embodiment of the invention the zwitterionic compound is a Zwitterionic detergent.

Other zwitterionic agents are sulfobetaines, including, for example, 3-(1-pyridino)-1-propane sulfonate, dimethyl-2-hydroxyethyl-1-propane sulfonate, 3-(1-methylpiperidinium)-1-propane sulfonate, dimethylbenzylammonium-1-propane sulfonate, dimethylethylammonium-1-propane sulfonate. Other zwitterionic agents include n-dodecyl-N,N-dimethylglycine, and lauryldimethylamine oxide.

About 0.1% to about 10% of a charged agent, such as a zwitterionic agent is added to the selective binding stock solution or working diluent. Therefore, about 0.02, 0.05, 0.1, 0.5, 1.0, 1.5, 2.0, 3.0, 4.0, 5.0, 6.0, 7.0, 8.0, 9.0, 10, 15, or 20% of a zwitterionic agent is present in a selective binding reaction.

A discriminating agent is an agent that allows selective binding of $PrP^{Sc}$ to a polyionic material, as described above, and/or prevents $PrP^c$ from binding to the polyionic material. The discriminating agent can have a lesser density of anionic groups than the polyionic material. The discriminating agent can be an anionic detergent, an amino acid amide of a fatty acid, or a laurylsarcosine. A discriminating agent can comprise about 0.5, 1.0, 2.0, 3.0, 4.0, 5.0, or 10% of the selective binding conditions.

Additionally, aptamers that are specific for $PrP^{Sc}$ can be used in the methods of the invention. Such aptamers are known in the art and are described in, e.g., Sayer et al., J. Biol. Chem. 279(13):13102 (2004); Rhie et al., J. Biol. Chem. 278(41)39697 (2003); Proske et al., Chembiochem. 3(8)717 (2002); Sekiya et al., Nucl. Acids Symp. Ser. 49, 361 (2005). "Selective binding" or "selective for" means that $PrP^{Sc}$ binds to an aptamer, while $PrP^c$ does not substantially bind the aptamer.

Furthermore, antibodies can interact with $PrP^{Sc}$ aggregates through non-specific paratope-independent interactions. See, e.g., Morel et al., J. Biol. Chem. 279(29):30143 (2004). Therefore, a rosetting effect can be achieved using antibodies of various specificities independently of the properties of their binding site. For selective aggregation of $PrP^{Sc}$ versus $PrP^c$ antibodies that do not recognize $PrP^c$ can be used. These antibodies can be identified efficiently by screening large libraries of antibodies of unrelated specificity in immunoprecipitation experiments. See id. at 30148. "Selective binding" or "selective for" means that $PrP^{Sc}$ binds to an antibody, while $PrP^c$ does not substantially bind antibody.

Examples of such antibodies include SAF-53; SAF-61; 12F10; Bar-234; SHA-31; 11C6; SHA-29; βS-43; βS-36; SHA-52; SHA-9; JEQ-254; His-2; EE-39; SDKP-21; His-22; and JEQ-255. See id. at 30144. These types of antibodies or combinations of these antibodies can be used in the methods of the invention.

Methods of Detection

Methods of the invention can be used to detect $PrP^{Sc}$ in a test sample, such as a leucocyte sample. The leucocyte sample can be from a mammal such as a bovine, ovine, mink, deer, elk, murine or human and other primates. A TSE or TSE infection can be diagnosed by contacting leucocytes from a subject with an antibody specific for $PrP^{Sc}$, an aptamer that selectively binds to $PrP^{Sc}$ and that does not substantially bind to $PrP^c$, a ligand that selectively binds to $PrP^{Sc}$ and that does not substantially bind to $PrP^c$, an antibody that selectively binds aggregates of $PrP^{Sc}$ but not $PrP^c$, wherein the antibody interacts with $PrP^{Sc}$ aggregates through non-specific paratope-independent interactions. The leucocytes are contacted with anti-immunoglobulin coated beads, such as magnetic beads. The anti-immunoglobulin can be anti-IgG or anti-IgM or other appropriate anti-isotype. The leucocytes, antibodies, aptamers, and/or ligands and beads can all be combined together at once or each component can be added sequentially. The beads and leucocytes are examined for a rosetting effect. A rosetting effect indicates a diagnosis of TSE. In another embodiment of the invention, leucocytes are contacted with beads that are coated with antibodies, aptamers, and/or ligands that are specific for or selective for $PrP^{Sc}$. The beads and leucocytes are examined for a rosetting effect. A rosetting effect indicates a diagnosis of TSE.

A rosetting effect occurs where about 5, 10, 20, or more leucocytes are attached to visible clumps of two or more beads as shown in FIG. 1A. The effect can be easily observed with a light microscope. The effect can also be observed or detected using other methods, e.g., flow cytometry (see, e.g., U.S. Pat. No. 6,784,981). Preferably, the examination is completed within 8, 12, 24, 36, or 48 hours of taking the sample from the subject.

The invention further comprises assay kits for diagnosing a TSE infection. A kit can comprises one or more antibodies aptamers, and/or ligands that bind $PrP^{Sc}$ and means for determining binding of the antibodies, aptamers, and/or ligands to leucocytes in the sample. The kit can also comprise packaging material comprising a label that indicates that the one or more antibodies, aptamers, and/or ligands of the kit can be used for the identification of TSE infection. Other components such as buffers, controls, and the like, known to those of ordinary skill in art, can be included in such test kits. The antibodies, aptamers, ligands, assays, and kits of the invention are useful, for example, in the diagnosis of individual cases of TSE infection in a patient, as well as epidemiological studies of TSE outbreaks.

Antibodies, aptamers, ligands, and assays of the invention can be combined with other polypeptides or assays to detect the presence of TSE along with other organisms.

The invention illustratively described herein suitably can be practiced in the absence of any element or elements, limitation or limitations that are not specifically disclosed herein.

Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above. All references cited in this disclosure are incorporated herein by reference.

EXAMPLES

Example 1

YYR-antibodies that bind $PrP^{Sc}$ have been used to demonstrate reactive epitopes on leucocytes (white blood cells) obtained from the blood of scrapie-infected sheep by flow cytometry. Isolated leucocytes are reacted with $PrP^{Sc}$-selective YYR-antibodies either labelled with a fluorescent marker or subsequently with labelled anti-isotype specific antibodies. Significant increases in cells bearing available YYR epitopes have been demonstrated in sheep developing scrapie. These diagnostic live leucocytes can be enriched from the general population using paramagnetic beads coated with YYR-antibodies.

In order to visualize this process, prepared leucocyte populations from sheep blood were reacted with YYR-antibodies attached directly to paramagnetic beads or separately followed by anti-immunoglobulin-coated beads and the resulting preparations examined under a light microscope.

In blood taken from scrapie-infected sheep between 12 and 15 months of age (with an expected disease termination of 22 to 27 months) a characteristic appearance has been noted. This consists of live leucocytes to which are attached visible clumps of beads as shown in FIG. 1. No or very few clumps of beads are associated with leucocytes from equivalent, matched, scrapie-free sheep.

This clumping, or "rosetting," is therefore a potential diagnostic for a live animal test for scrapie, in the pre-clinically affected patient.

Example 2

Leucocytes were extracted from whole blood. $PrP^{Sc}$-expressing cells present in scrapie positive sheep (as confirmed by ImmunoCapillary Electrophoresis, ICE, and by histopathology following post-mortem examination of the brain), were immunoprecipitated and compared to scrapie negative samples. Immunoprecipitation was carried out using $PrP_{Sc}$ selective YYR antibody 31A.8 from IDEXX Laboratories (the hybridoma producing 31A.8 is deposited under the Budapest Treaty at American Type Culture Collection (ATCC), 10801 University Boulevard Manassas, Va. 20110-2209 as PTA-7393; the deposit will be maintained under the terms of the Budapest Treaty on the International Recognition of the Deposit of Microorganisms and all restrictions imposed by the depositor on the availability to the public of the deposited material will be irrevocably removed upon the granting of the patent) as this antibody had shown best suitability for ovine material in previous tests.

Initial observations of scrapie suspect blood (citrated from INRA, France and EDTA from Ripley, VLA) and scrapie unexposed EDTA blood from Grange, VLA, using 31A.8 coated tosyl-activated magnetic Dynal beads, showed inconsistent results for positive and negative samples. There were very few leucocytes and both positive and negative samples showed association of leucocytes with beads. However, when the leucocytes were incubated with non-immobilised anti-$PrP^{Sc}$ antibody in solution prior to being incubated with anti-mouse IgM coated magnetic beads, the results improved and a significant enrichment was seen by FACS analysis (5% of total to 71% of total cells).

It was suggested that this immunoenrichment could be confirmed by examination of the beads by light microscopy to demonstrate aggregation or clumping of cells. The microscope slides looked very promising and all samples from scrapie positive animals showed rosetting of leucocytes pre-incubated with YYR antibody associated with the anti-IgM coated magnetic beads. This indicated that the IDEXX anti-$PrP^{Sc}$ antibody, 31A.8, had bound to cell surface $PrP^{Sc}$ on leucocytes and the magnetic anti-IgM coated beads had bound to the anti-PrP IgM antibody. Most samples from negative animals showed isolated unassociated magnetic beads with few isolated leucocytes. Preparations were viewed by eye under a microscope. See FIG. 1. The scrapie-positive sample was from a 12 month old VRQ/VRQ genotype which subsequently developed scrapie at 23 months.

Example 3

The viability of leucocytes preparations and changes in binding of 31A.8 to cell surface $PrP^{Sc}$ and anti-IgM coated paramagnetic beads over time with leucocyte "apoptosis."

Blood was taken from four 18 months old VRQ homozygous sheep that had at 1 month of age been inoculated subcutaneously with 1 g of brain homogenate derived from scrapie-infected sheep at terminal disease. The sheep were isolated (at Grange Farm) for the Veterinary Laboratories Agency (VLA), Weybridge, UK. Four sheep from a non-exposed, scrapie-free flock also at the VLA were used as negative controls.

Preparation of cell suspensions: All ovine blood samples were obtained by jugular venipuncture with EDTA syringes and processed by density gradient centrifugation. Blood from scrapie free sheep was used as a source for negative control peripheral blood leucocytes. The number of cells was estimated to $1 \times 10^6$ cells/ml of blood. All procedures were carried out at 4° C. and all washes and suspensions were in phosphate-buffered saline (Dulbecco's stock solution, Sigma, Poole, UK) with either 5% or 0.1% bovine serum albumin (Sigma, Poole, UK). Peripheral blood was separated from 1:1 RPMI diluted (Sigma, Poole, UK) whole blood by density gradient centrifugation (2500 rpm, 20 min Histopaque-1077 [specific gravity 1.077±0.001 g/ml], Sigma-Aldrich, Poole, UK). The leucocyte layer was taken from above the interface and cells were washed in phosphate-buffered saline (PBS)

Dulbecco's stock solution, Sigma, Poole, UK) (200×g, 10 min) and then resuspended in phosphate buffered saline with 5% bovine serum albumin (BSA) Sigma, Poole, UK).

Light microscopy. 20 μg of anti-YYR MAb 31A.8 was added to cells and incubated with rotation at 4° C. over night. Cells were washed in 50 ml of phosphate buffered saline and 0.1% bovine serum albumin and pelleted by centrifugation (322×g, 7 min). 25V of anti-IgM beads that had been washed twice with PBS and 0.1% BSA were added and incubated for 15 minutes at room temperature with mixing. Cells were washed three times with PBS and 0.1% BSA in a magnetic particle concentrator (MPC). After final wash, cells were transferred to a microscope slide and observed by bright field microscopy (Leica) with the addition of Trypan blue.

31A.8 coated magnetic beads bind leucocytes from blood of scrapie infected sheep but not control sheep. Non-immobilised 31A.8 antibody and anti-IgM coated magnetic beads were incubated with isolated leucocytes from four scrapie exposed (samples labelled with suffix SV), and four control sheep blood (Suffix ST) to demonstrate binding to the cell surface of leucocytes. The experiment was carried out over the space of seven days on the same set of blood samples. Cells binding 31A.8 coated beads were identified only in blood of scrapie exposed sheep by light microscopy in all of the scrapie positive sheep on day one. The number of rosettes visible were only a small percentage of the total population of leucocytes (consistent with FACS analysis) indicating that 31A.8 binding cells are rare. In addition, it appears that most rosettes are formed around non-viable cells although, some viable cells also showed bead association (See Table 1). By day two, both negative and positive samples showed rosetting but both categories showed a very small amount of rosetting overall. By day three, the number of rosettes had increased in both scrapie suspect and scrapie unexposed sheep. Most rosettes at this stage appeared to be associated with apoptotic cells. By day four, it appeared that the negative cells attract more rosetting (See Table 1.) All samples showed an increase in unassociated non-viable cells with time. In addition, scrapie suspect cells appeared to bind less beads with time and most rosettes seen in these samples only contained between 2-5 bead rosettes compared to 5+ in the negative samples.

TABLE 1

An approximate number of rosettes per slide with number of live cells in brackets. Leucocytes were prepared on day 0 and cells were analysed by light microscopy one day after leucocyte preparation (day 1), four days after leucocyte preparation (day 2), five days after leucocyte preparation (day 3) and, six days after leucocyte preparation (day 4).

|        | Day 1     | Day 2  | Day 3     | Day 4   |
|--------|-----------|--------|-----------|---------|
| ST1728 | 0         | ~10    | 10-20     | ~40     |
| ST1729 | 0         | 1      | 5-10      | ~20 (1) |
| ST1733 | 0         | 2      | 10-20     | ~10 (2) |
| ST1739 | 0         | 0      | ~5 (1)    | ~10     |
| SV2260 | 5-10 (~5) | 1      | 20-25 (~5)| ~10 (1) |
| SV2274 | 10-20 (~5)| ~3     | 20-30     | ~10 (1) |
| SV2276 | 20 (~5)   | ~5 (2) | 5-10      | ~5      |
| SV2281 | 10-20 (~5)| 5-10   | ~5        | ~10     |

Initial observations from the blood of sheep from a scrapie endemic flock using a resetting technique with 31A.8 mAb indicated rare positive cells in sheep incubating disease. Further observations on blood from sheep from scrapie exposed and unexposed sheep were carried out. Observations on day 1 already indicated that most rosettes were formed around non-viable cells although there were still some viable cell rosettes. On day two, rosettes had formed in both negative and positive samples indicating that 31A.8 binds non-specifically to apoptotic cells. These observations are supported by observations of 31A.8 staining on leucocytes analysed by flow cytometry where data revealed that 31A.8 binds a large amount of non-viable cells. Rosetting in negative samples seem to increase with time whereas in positive samples, there seem to be a peak at day 3 followed by a reduction in number of rosettes. It was also observed that the rosettes associated with scrapie suspect cells often contained a smaller number of beads than the rosettes seen associated with scrapie unexposed cells.

These observations indicate a difference in negative and positive samples on blood up to one day old however, there is already a fairly large amount of non-viable resetting at this stage. It appears that the age of the blood is very important in being able to distinguish between positive and negative leucocytes using this technique. It also appears that scrapie exposed sheep blood cells apoptose at an earlier stage than leucocytes from negative sheep. This may indicate a connection between cell surface $PrP^{Sc}$ and cell apoptosis.

Example 4

It is apparent that there is a difference between negative and positive samples using this technique but also that this difference diminishes with time. In order to investigate this trend further it would be necessary to test the blood on the same day as the cell suspension is prepared and then to test the cells every day for five or so days. It is also necessary to generate more quantitative data using for example a haemocytometer or by just adding a grid to the normal microscope slide and then count all the cells, with and without associated beads, on the whole slide.

Results from previous experiments using 31A.8 mAb and anti-IgM coated paramagnetic beads showed beads binding to cells in positive but not in negative blood. It also appears that the number of rosettes to non-viable cells increase with time. In order to investigate further, another experiment was set up which used an RBC-lysis method and a repeated density centrifugation step.

Method

Sheep: Blood was taken from two 19 months old VRQ homozygous sheep that had at 1 month of age been inoculated sub-cutaneously with 1 g of brain homogenate derived from infected sheep and two 9 months old sheep from a scrapie saturated flock. The inoculated sheep were kept at Grange Farm and the saturated flock is kept in Ripley for the Veterinary Laboratories Agency (VLA), Weybridge, UK. Four sheep from a scrapie free flock also at the VLA were used as negative controls.

Preparation of cell suspensions: All ovine blood samples were obtained by jugular venipuncture with EDTA syringes and processed by a buffy coat and red cell lysis technique on day 1. Blood from scrapie free sheep was used as a source for negative control peripheral blood leucocytes. The number of cells was estimated to $1 \times 10^6$ cells/ml of blood. All procedures were carried out at 4° C. and all washes and suspensions were in phosphate-buffered saline (Dulbecco's stock solution, Sigma, Poole, UK) with either 5% or 0.1% bovine serum albumin (Sigma, Poole, UK). Whole blood was spun in 10 ml EDTA tubes at 895×g for 20 minutes. Cells were drawn from the buffy coat above the red blood cell layer, washed in 10 ml of lysis buffer twice (155 mM $NH_4Cl$, 10 mM $NaHCO_3$) by centrifugation (322×g, 10 min), and resuspended in 0.5 ml of wash buffer. Prior to use on Day 2 and onwards, non-viable cells were separated from cell suspension by density gradient centrifugation (2500 rpm, 20 min Histopaque-1077 [specific gravity 1.077±0.001 g/ml], Sigma-Aldrich, Poole, UK). The leucocyte layer was taken from above the interface and cells were washed in phosphate-buffered saline ((PBS) Dulbecco's stock solution, Sigma, Poole, UK) with 0.1% bovine albumin serum (and 1% sarkosyl on day 5 only) (200×g, 10 min) and then resuspended in 0.5 ml of phosphate buffered saline with 5% bovine serum albumin ((BSA) Sigma, Poole, UK).

Figure 2:
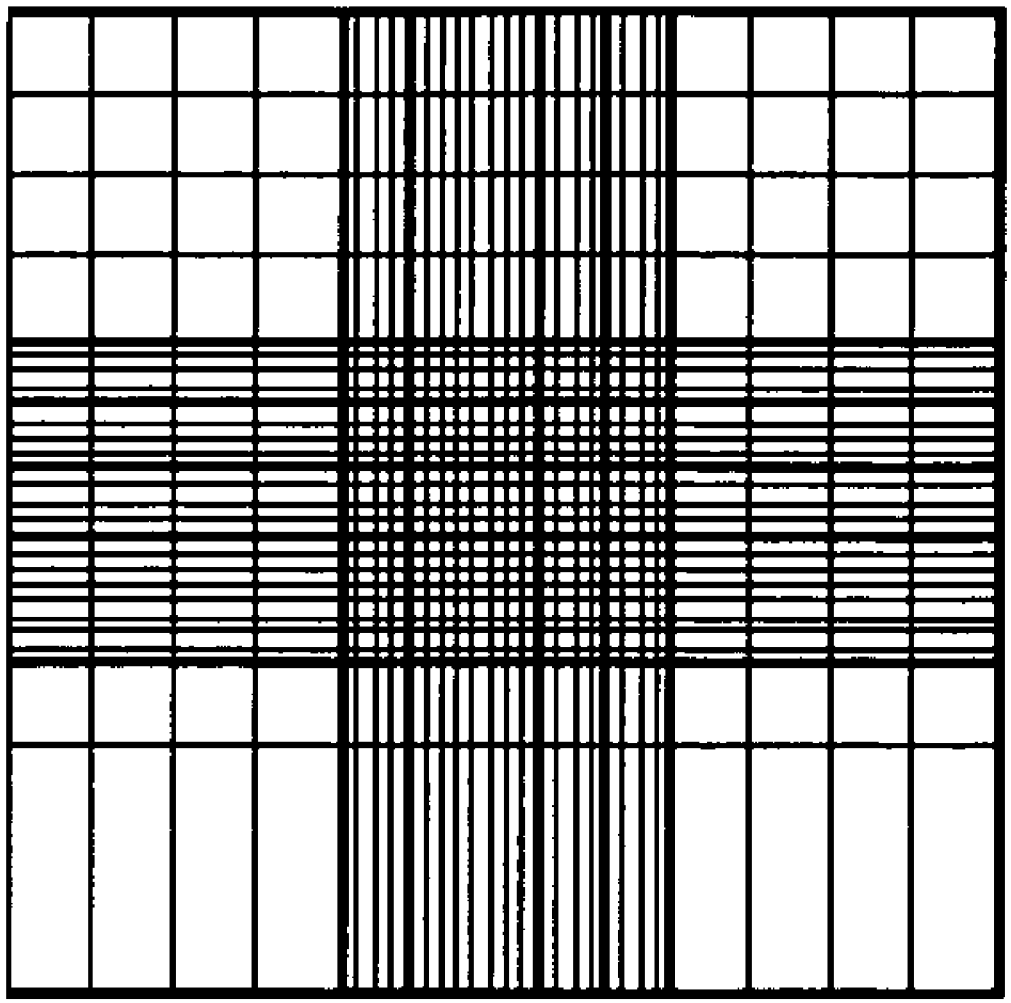
FIG. 2 shows a diagram of the slides used to examine the rosetting effect. All squares within the circle were counted when analysing Dynabeads associated with peripheral leucocytes.

Light microscopy. 40 μg of anti-YYR MAb 31A.8 was added to cells and incubated with rotation at 4° C. for 30 minutes. Cells were washed in 1 ml of phosphate buffered saline and 0.1% bovine serum albumin and pelleted by centrifugation (1300 rpm, 4 min). 25 μl of anti-IgM beads (Tysolactivated magnetic Dyna beads coated with anti-mouse IgM according to manufacturer's instructions) that had been washed twice with PBS and 0.1% BSA were added and incubated for 15 minutes at room temperature while mixing. Cells were washed three times with PBS and 0.1% BSA in a magnetic particle concentrator (MPC). After the final wash, 6 μl of cells were transferred to a haemocytometer slide (see FIG. 2) and observed by bright field microscopy (Leica) with the addition of 4 μl of Trypan blue.

Results 31A.8 and anti-IgM coated magnetic beads bind leucocytes from blood of scrapie infected sheep but not control sheep.

Non-immobilized 31A.8 and anti-IgM coated magnetic beads were incubated with isolated leucocytes from four scrapie exposed and four control sheep blood to demonstrate binding to the cell surface of leucocytes. The experiment was carried out over the space of five days on the same set of bloods (Monday-Friday).

TABLE 2

Number of bead rosettes × $10^5$ per ml of sample

| Animal Number | Day 1 (cells/ml) | | Day 2 (cells/ml) | | Day 3 (cells/ml) | | Day 4 (cells/ml) | | Day 5 (cells/ml) | |
|---|---|---|---|---|---|---|---|---|---|---|
| W1625 | Viable | 0 | Viable | 1.5 | Viable | 0 | Viable | 3 | Viable | 0 |
| | Apoptotic | 7.5 | Apoptotic | 1.5 | Apoptotic | 4.5 | Apoptotic | 1.5 | Apoptotic | 0 |
| W1651 | Viable | 3 | Viable | 3 | Viable | 1.5 | Viable | 0 | Viable | 0 |
| | Apoptotic | 4.5 | Apoptotic | 1.5 | Apoptotic | 3 | Apoptotic | 0 | Apoptotic | 0 |
| W1652 | Viable | 0 | Viable | 1.5 | Viable | 12 | Viable | 0 | Viable | 0 |
| | Apoptotic | 4.5 | Apoptotic | 0 | Apoptotic | 7.5 | Apoptotic | 4.5 | Apoptotic | 0 |
| W1654 | Viable | 1.5 | Viable | 4.5 | Viable | 6 | Viable | 0 | Viable | 0 |
| | Apoptotic | 0 | Apoptotic | 0 | Apoptotic | 4.5 | Apoptotic | 6 | Apoptotic | 0 |
| <u>SV2270</u> | Viable | 0 | Viable | 0 | Viable | 0 | Viable | 7.5 | Viable | 0 |
| | Apoptotic | 6 | Apoptotic | 3 | Apoptotic | 1.5 | Apoptotic | 3 | Apoptotic | 0 |
| <u>SV2576</u> | Viable | 1.5 | Viable | 12 | Viable | 0 | Viable | 4.5 | Viable | 0 |
| | Apoptotic | 0 | Apoptotic | 4.5 | Apoptotic | 3 | Apoptotic | 13.5 | Apoptotic | 0 |
| <u>SW1169</u> | Viable | 4.5 | Viable | 3 | Viable | 7.5 | Viable | 1.5 | Viable | 0 |
| | Apoptotic | 0 | Apoptotic | 3 | Apoptotic | 10.5 | Apoptotic | 4.5 | Apoptotic | 0 |
| <u>SW1298</u> | Viable | 7.5 | Viable | 3 | Viable | 4.5 | Viable | 3 | Viable | 0 |
| | Apoptotic | 6 | Apoptotic | 3 | Apoptotic | 3 | Apoptotic | 0 | Apoptotic | 0 |

Table 2 shows the number of bead-cell associations to viable and apoptotic cells×$10^5$ per 1 ml of sample. To determine the rosette density of the sample, Number of rosettes=number counted×number of squares (25)×dilution×$10^4$. Bold represents scrapie unexposed sheep and underlining, scrapie exposed sheep.

TABLE 3

Number of unassociated viable and apoptotic cells × $10^5$ per ml of sample

| Animal number | Day 1 (cells/ml) | | Day 2 (cells/ml) | | Day 3 (cells/ml) | | Day 4 (cells/ml) | | Day 5 (cells/ml) | |
|---|---|---|---|---|---|---|---|---|---|---|
| W1625 | Viable | 6 | Viable | 0 | Viable | 1.5 | Viable | 1.5 | Viable | 0 |
| | Apoptotic | 6 | Apoptotic | 1.5 | Apoptotic | 0 | Apoptotic | 0 | Apoptotic | 0 |
| W1651 | Viable | 4.5 | Viable | 0 | Viable | 0 | Viable | 0 | Viable | 0 |
| | Apoptotic | 4.5 | Apoptotic | 0 | Apoptotic | 0 | Apoptotic | 0 | Apoptotic | 0 |
| W1652 | Viable | 0 | Viable | 0 | Viable | 1.5 | Viable | 0 | Viable | 0 |
| | Apoptotic | 4.5 | Apoptotic | 0 | Apoptotic | 4.5 | Apoptotic | 3 | Apoptotic | 0 |
| W1654 | Viable | 1.5 | Viable | 1.5 | Viable | 1.5 | Viable | 1.5 | Viable | 0 |
| | Apoptotic | 3 | Apoptotic | 0 | Apoptotic | 3 | Apoptotic | 3 | Apoptotic | 0 |
| <u>SV2270</u> | Viable | 3 | Viable | 0 | Viable | 0 | Viable | 0 | Viable | 0 |
| | Apoptotic | 13.5 | Apoptotic | 0 | Apoptotic | 1.5 | Apoptotic | 3 | Apoptotic | 0 |
| <u>SV2576</u> | Viable | 7.5 | Viable | 0 | Viable | 0 | Viable | 1.5 | Viable | 0 |
| | Apoptotic | 1.5 | Apoptotic | 0 | Apoptotic | 1.5 | Apoptotic | 6 | Apoptotic | 0 |
| <u>SW1169</u> | Viable | 16.5 | Viable | 1.5 | Viable | 0 | Viable | 1.5 | Viable | 0 |
| | Apoptotic | 60 | Apoptotic | 0 | Apoptotic | 3 | Apoptotic | 1.5 | Apoptic | 0 |
| <u>SW1298</u> | Viable | 1.5 | Viable | 0 | Viable | 0 | Viable | 3 | Viable | 0 |
| | Apoptotic | 9 | Apoptotic | 0 | Apoptotic | 4.5 | Apoptotic | 1.5 | Apoptotic | 0 |

Table 3 shows the number of unassociated viable and apoptotic cells×$10^5$ per 1 ml of sample. To determine the cell density of the sample, Number of rosettes=number counted× number of squares (25)×dilution×$10^4$. Bold represents scrapie unexposed sheep and underlining, scrapie exposed sheep.

Figure 3:
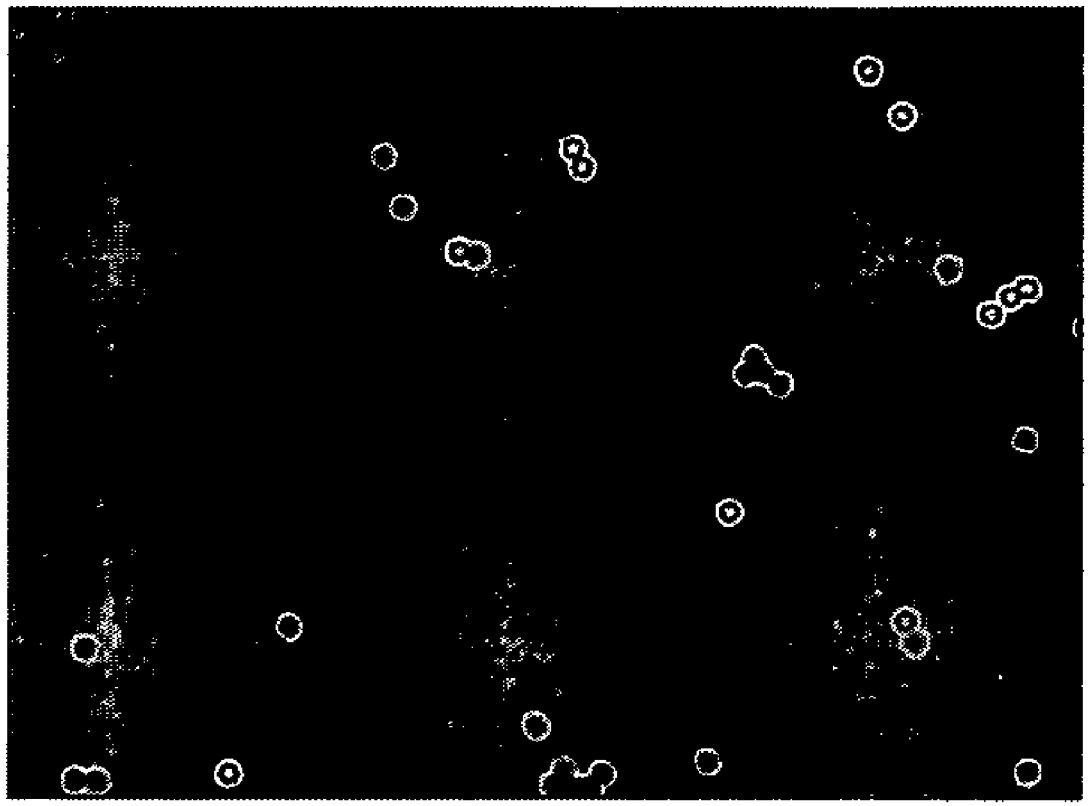
FIG. 3 shows a photograph of a light microscope slide of leucocytes from one animal from the scrapie inoculated Grange study at ×40 magnification. 31A.8 binding to apoptotic cells demonstrated by the rosetting of beads to cell surface $PrP^{Sc}$ on Trypan blue stained scrapie positive leucocytes.

Cells binding anti-IgM coated beads were identified in blood by light microscopy in all of the sheep on day one. See FIG. 3. Both negative and positive samples were showing rosetting to both viable and non-viable cells and there does not appear to be a particular trend. The same was observed for day 2, 3 and 4 without any particular pattern appearing. On day 5, there were no viable cells present in the sample any longer so no binding or unassociated cells were observed. The only distinguishing factor with this time course study seem to be the fact that positive samples appeared to contain a larger amount of congregated beads.

Initial observations from blood of sheep from a scrapie endemic flock using a resetting technique with 31A.8 mAb indicated rare positive cells in sheep. Further observations on blood from sheep from scrapie exposed and unexposed sheep were carried out. Observations indicated a difference between positive and negative samples but also that most rosettes were formed around non-viable cells although there were still some viable cell rosettes. Rosettes formed in both negative and positive samples with time indicating that 31A.8 binds non-specifically to apoptotic cells. These observations are supported by observations of 31A.8 staining on leucocytes analysed by flow cytometry where data revealed that 31A.8 binds a large amount of non-viable cells. It was also observed that the rosettes associated with scrapie suspect cells often contained a smaller number of beads than the rosettes seen associated with scrapie unexposed cells. These initial observations indicate a difference between bead association in negative and positive peripheral blood samples but further observations carried out during a time period of 5 days show no such difference.

We claim:

1. A method for detecting a transmissible spongiform encephalopathy (TSE) agent comprising:
    (a) contacting isolated leucocytes from a subject with an antibody selective for $PrP^{Sc}$, wherein the antibody is produced by hybridoma ATCC PTA-7393;
    (b) contacting the isolated leucocytes with anti-immunoglobulin coated beads;
    (c) examining the beads and leucocytes for a rosetting effect;
    wherein a rosetting effect indicates detection of the TSE agent.

2. The method of claim 1, wherein the subject has no TSE symptoms.

3. The method of claim 1, wherein the subject is a human, non-human primate, ovine, bovine, deer, elk, murine or mink.

4. A method for detecting transmissible spongiform encephalopathy (TSE) agents comprising:
    (a) contacting isolated leucocytes from a subject with beads, wherein the beads are coated with antibodies that are selective for $PrP^{Sc}$, wherein the antibodies are produced by hybridoma ATCC PTA-7393;
    (b) examining the beads and isolated leucocytes for a rosetting effect;
    wherein a rosetting effect indicates detection of TSE agents.

5. The method of claim 4, wherein the subject has no TSE symptoms.

6. The method of claim 4, wherein the subject is a human, non-human primate, ovine, bovine, deer, elk, murine or mink.

* * * * *

UNITED STATES PATENT AND TRADEMARK OFFICE
CERTIFICATE OF CORRECTION

PATENT NO. : 7,601,506 B2
APPLICATION NO. : 11/494964
DATED : October 13, 2009
INVENTOR(S) : Jackman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 35 days.

Signed and Sealed this

Fifth Day of October, 2010

David J. Kappos
*Director of the United States Patent and Trademark Office*